(12) United States Patent
Burriesci et al.

(10) Patent No.: US 8,034,103 B2
(45) Date of Patent: Oct. 11, 2011

(54) ANNULOPLASTY PROSTHESIS WITH AN AUXETIC STRUCTURE

(75) Inventors: Gaetano Burriesci, Palermo (IT); Giovanni Bergamasco, Turin (IT)

(73) Assignee: Sorin Biomedica Cardio S.r.l., Saluggia (Vercelli) (IT)

( * ) Notice: Subject to any disclaimer, the term of this patent is extended or adjusted under 35 U.S.C. 154(b) by 79 days.

(21) Appl. No.: 11/617,026

(22) Filed: Dec. 28, 2006

(65) Prior Publication Data
US 2007/0162112 A1 Jul. 12, 2007

(30) Foreign Application Priority Data
Dec. 28, 2005 (EP) .................................... 05425926

(51) Int. Cl.
*A61F 2/24* (2006.01)
(52) U.S. Cl. ...................................... 623/2.36; 623/2.37
(58) Field of Classification Search ................. 623/2.36, 623/2.37
See application file for complete search history.

(56) References Cited

U.S. PATENT DOCUMENTS

| | | | |
|---|---|---|---|
| 3,656,185 A | 4/1972 | Carpentier | |
| 4,055,861 A | 11/1977 | Carpentier et al. | |
| 4,917,698 A | 4/1990 | Carpentier et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,084,151 A | 1/1992 | Vallana et al. | |
| 5,104,407 A | 4/1992 | Lam et al. | |
| 5,133,845 A | 7/1992 | Vallana et al. | |
| 5,370,684 A | 12/1994 | Vallana et al. | |
| 5,387,247 A | 2/1995 | Vallana et al. | |
| 5,423,886 A | 6/1995 | Arru et al. | |
| 5,607,471 A | 3/1997 | Seguin et al. | |
| 5,674,279 A | 10/1997 | Wright et al. | |
| 5,716,397 A | 2/1998 | Myers | |
| 5,824,066 A | 10/1998 | Gross | |
| 5,873,812 A | 2/1999 | Ciana et al. | |
| 6,102,945 A | 8/2000 | Campbell | |
| 6,106,550 A | 8/2000 | Magovern et al. | |
| 6,143,024 A | 11/2000 | Campbell et al. | |
| 6,217,610 B1 | 4/2001 | Carpentier et al. | |
| 6,250,308 B1 | 6/2001 | Cox | |
| 6,309,414 B1 | 10/2001 | Rolando et al. | |
| 6,406,493 B1 | 6/2002 | Tu et al. | |
| 6,565,603 B2 | 5/2003 | Cox | |

(Continued)

FOREIGN PATENT DOCUMENTS
EP 0338994 10/1989
(Continued)

OTHER PUBLICATIONS
European Search Report for EP 05425926.2, 4 pp.
(Continued)

*Primary Examiner* — David Isabella
*Assistant Examiner* — Jason-Dennis Stewart
(74) *Attorney, Agent, or Firm* — Faegre & Benson LLP

(57) ABSTRACT

An annuloplasty prosthesis including an inner tubular member having a lateral wall and exhibiting auxetic behavior when subject to a tensile stress along the longitudinal axis of at least one of its portions. The auxetic behavior may be obtained by perforating the tubular member with apertures of desired shape, thus obtaining, for instance, re-entrant honeycomb cell structures or cell structures with two-dimensional chiral symmetry.

15 Claims, 6 Drawing Sheets

U.S. PATENT DOCUMENTS

| | | |
|---|---|---|
| 6,749,630 B2 | 6/2004 | McCarthy et al. |
| 6,797,001 B2 | 9/2004 | Mathis et al. |
| 7,226,477 B2 | 6/2007 | Cox |
| 2001/0021874 A1 | 9/2001 | Carpentier et al. |
| 2002/0010504 A1 | 1/2002 | Alt |
| 2002/0188350 A1 | 12/2002 | Arru et al. |
| 2003/0199974 A1 | 10/2003 | Lee et al. |
| 2003/0208264 A1 | 11/2003 | McCarthy et al. |
| 2003/0208284 A1 | 11/2003 | Stewart et al. |
| 2003/0220686 A1* | 11/2003 | Arru et al. .................... 623/2.36 |
| 2004/0039443 A1* | 2/2004 | Solem et al. ................. 623/2.37 |
| 2004/0249453 A1 | 12/2004 | Cartledge et al. |
| 2006/0129227 A1* | 6/2006 | Hengelmolen .............. 623/1.16 |
| 2007/0191940 A1 | 8/2007 | Arru et al. |

FOREIGN PATENT DOCUMENTS

| | | |
|---|---|---|
| EP | 1266641 | 12/2002 |
| EP | 1348406 B1 | 12/2009 |
| SU | 577022 A1 | 10/1977 |
| WO | 2005072649 A | 8/2005 |

OTHER PUBLICATIONS

European Search Report for EP 01830378.4, 3 pages.
European Search Report for EP 02425190.2, 3 pages.

* cited by examiner

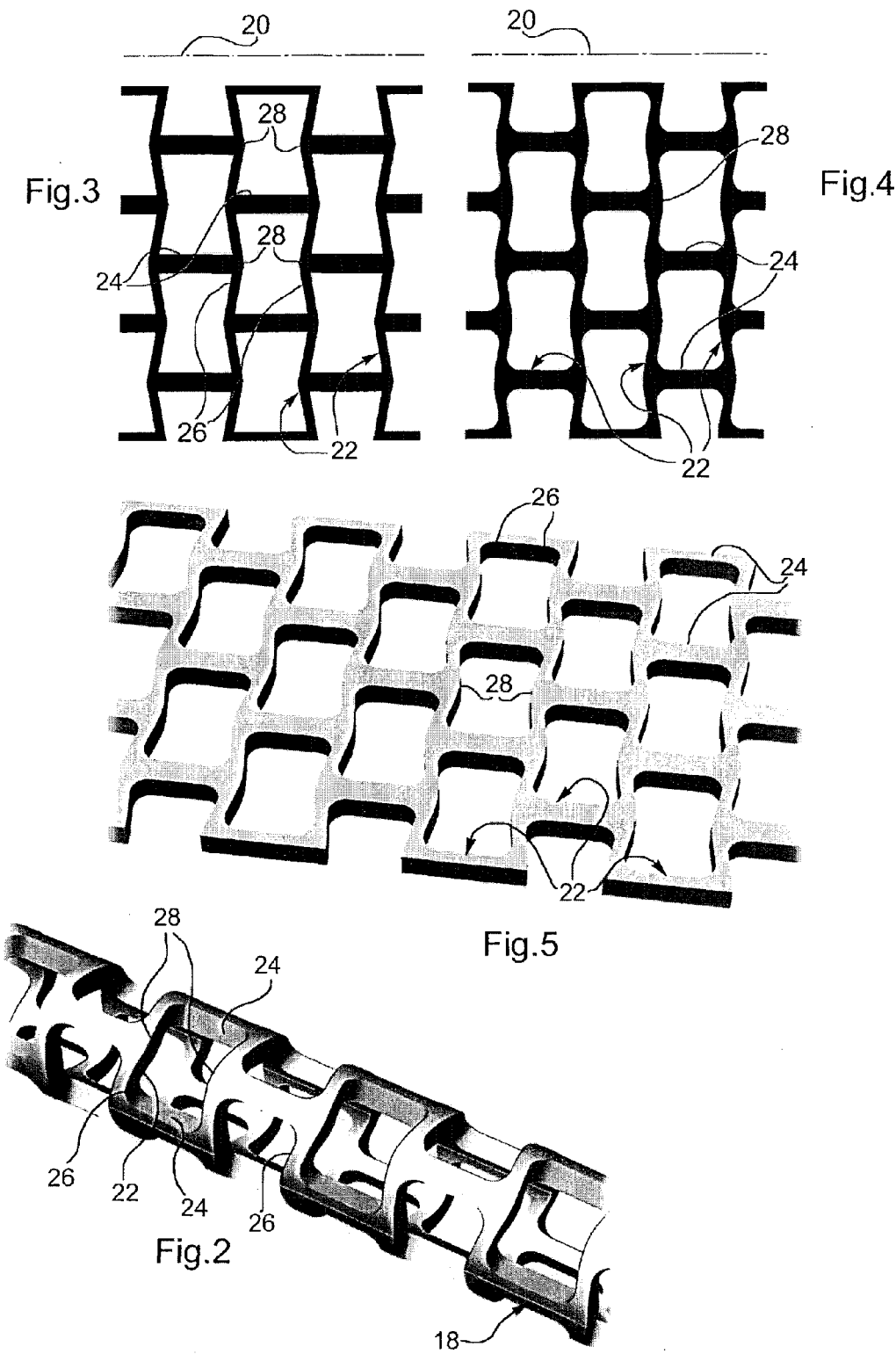

Fig. 11
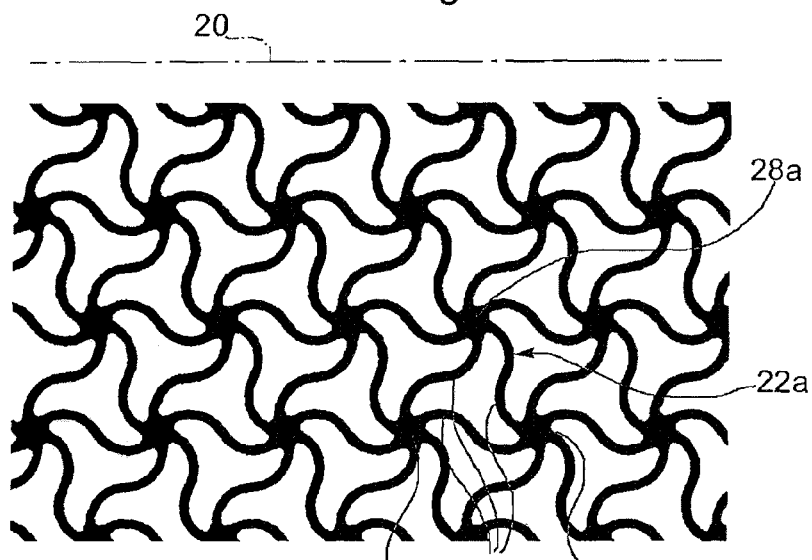
Fig. 12
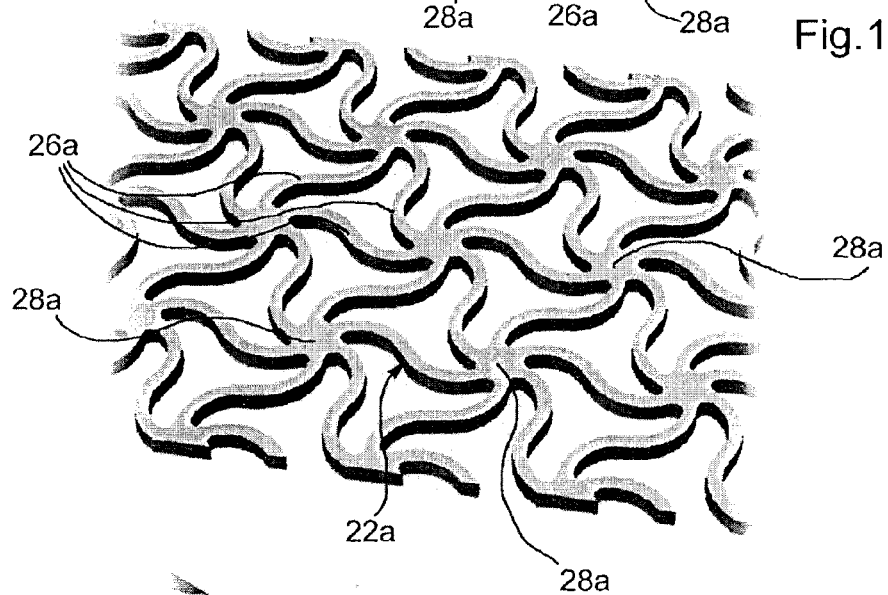
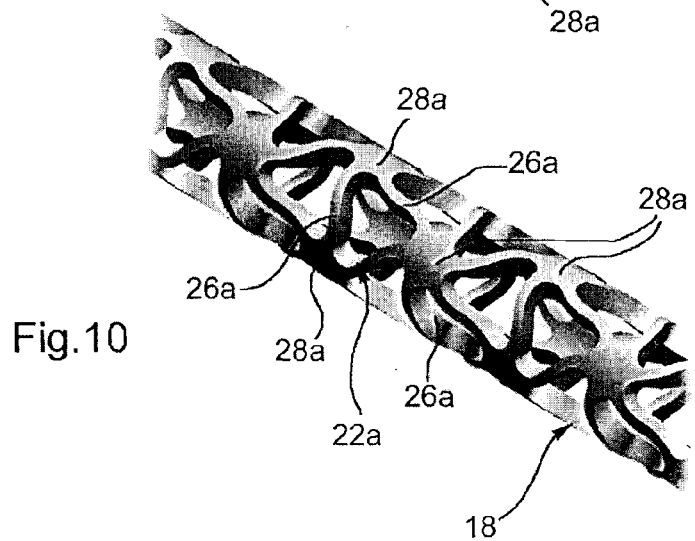
Fig. 10

ANNULOPLASTY PROSTHESIS WITH AN AUXETIC STRUCTURE

CROSS REFERENCE TO RELATED APPLICATION

This application claims priority from European Patent application No. 05425926.2, filed Dec. 28, 2005, which is incorporated herein by reference for all purposes.

TECHNICAL FIELD

The present invention relates in general to a device for cardiac valve repair surgery, and, in particular, to an annuloplasty prosthesis.

BACKGROUND

The human heart has four cardiac valves: the mitral valve, the tricuspid valve, the pulmonary valve and the aortic valve. The mitral valve is situated in the left atrioventricular ostium and ensures that the blood flows in one direction from the atrium to the ventricle. It opens in the diastoles and closes in the systoles, preventing the blood from flowing back from the ventricle to the atrium. The shape, dimensions and flexibility of the annulus of a normally functioning mitral valve are such as to enable the valve lips to close correctly during the systolic phase. The mitral annulus has, for instance, a characteristic "kidney" (or "D") shape and is more flexible in the portion corresponding to the posterior lip of the valve. Diseases and genetic defects may cause the annulus of the mitral valve to be deformed or dilated with the result that it does not close completely and there is therefore a regurgitation of blood. This problem may also occur in the tricuspid valve situated between the right atrium and the right ventricle.

A method frequently used to eliminate some pathological impairments of the mitral and tricuspid valves is to return the valve annulus to its correct shape and dimensions by surgical procedures known as annuloplasty.

Annuloplasty consists in the surgical implantation of a support prosthesis on the dilated or deformed annulus, in order to return it to its physiological shape and/or dimensions so that the cardiac valve can function correctly. The support prostheses used in valve repair surgery are known as annuloplasty prostheses. In most cases, these prostheses are formed by a closed or open ring structure comprising an inner ring-shaped member and an outer coating of biocompatible material which enables its surgical suturing.

Various kinds of annuloplasty prostheses have been disclosed in the prior art. Prostheses whose rigidity may be made variable in a desired manner depending on the point, the direction and/or the method of application of stresses are in particular already known. For instance, U.S. Publication 2003/0220686 discloses various embodiments of an annuloplasty prosthesis comprising an inner tubular member having a plurality of apertures in at least one portion of its wall.

SUMMARY

The present invention provides an annuloplasty prosthesis comprising an inner member provided with optimum properties of bending stability during both production and use, and adapted to be bent according to radii of curvature which may also be very small. According to an embodiment of the present invention, this is achieved by an annuloplasty prosthesis for implantation in a cardiac valve annulus, the prosthesis comprising a tubular member having a size and shape generally corresponding to a shape of the cardiac valve annulus and includes a longitudinal axis, a straight section having first and second ends, and a first curved section between the first and second ends. At least the first curved section includes a plurality of columns of cells disposed along the longitudinal axis such that at least the first curved section exhibits an auxetic behavior when subject to a tensile stress along the longitudinal axis.

The present invention, according to another embodiment, is a method of manufacturing an annuloplasty prosthesis, the method comprising forming a plurality of columns of cells having a first size and shape in at least a portion of a tube such that the portion of the tube exhibits an auxetic behavior, and bending the tube to form a straight section having first and second ends, and a first curved section between the first and second ends. The step of bending the tube causes cells in at least the first curved section to assume a second size and shape.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

Further characteristic features and advantages of the invention are set out in the following detailed description, given purely by way of non-limiting example and made with reference to the accompanying drawings, in which:

FIG. 2 is a perspective view of a portion of a tubular member of the prosthesis of FIG. 1;

FIG. 3 is a plan view of the plane development of the member of FIG. 2 with schematic geometry;

FIG. 4 is a view similar to FIG. 3 with non-schematic geometry;

FIG. 5 is a perspective view of the plane development of the tubular member of FIG. 2;

FIGS. 10 to 12 are views corresponding respectively to FIGS. 2, 4 and 5 of a particular embodiment of the tubular member of the prosthesis of the invention of the general type shown in FIG. 9.

Figure 1:
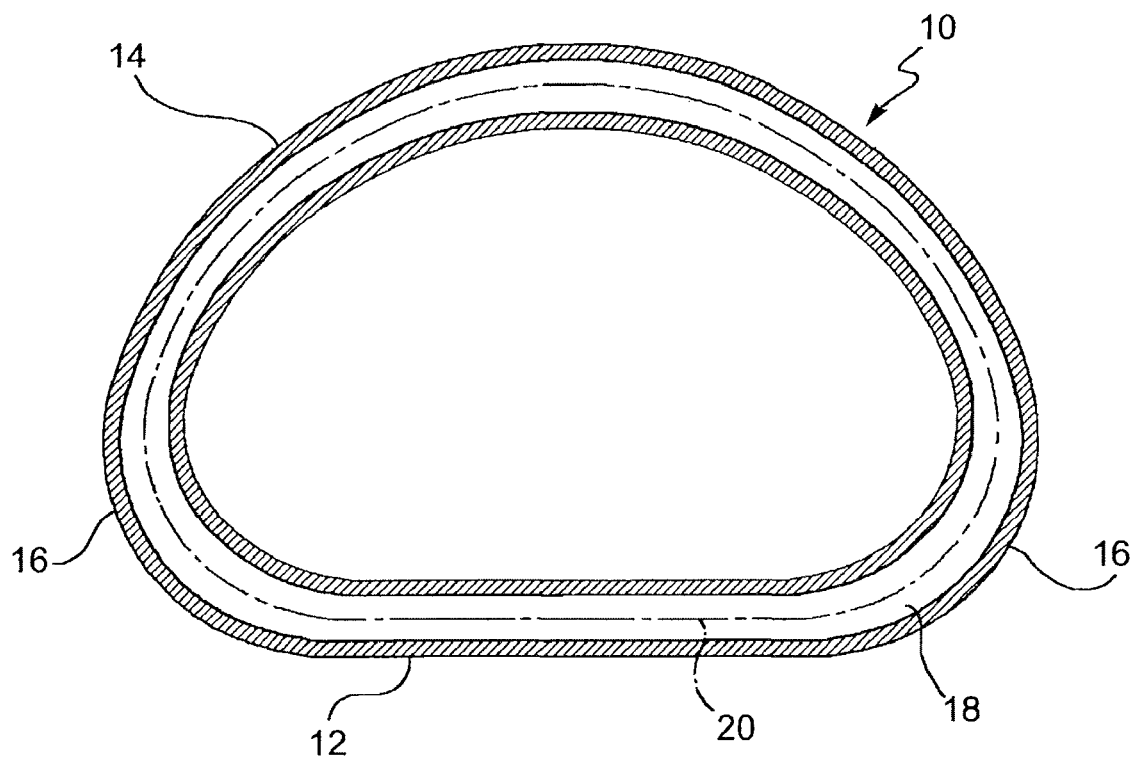
FIG. 1 is a diagrammatic plan view of a prosthesis of the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

An annuloplasty prosthesis 10 (FIG. 1) has a shape generally reproducing the geometry of the annulus of a mitral valve, i.e. it is a D-shaped closed ring. This ring comprises an approximately rectilinear (i.e., straight) intertrigonal section 12, a first curved section 14 facing the rectilinear section 12 and two second curved sections 16, whose curvature is more accentuated than the first curved section 14, which connect the latter to the end of the rectilinear intertrigonal section 12. As will be explained in detail below, one or more portions of the annuloplasty prosthesis 10, e.g., at least the first curved section 14, are configured to advantageously exhibit an auxetic behavior when subjected to a tensile stress along the longitudinal axis.

A structure with auxetic behavior, such as the annuloplasty prosthesis 10 of the present invention, is understood to be a structure which, when it is subject to a tensile stress in one direction, expands in a direction perpendicular to the direction in which the stress is applied, and which, when it is subject to a compression stress in one direction, contracts again in a direction perpendicular to the direction in which the stress is applied. This concept may also be expressed by saying that the structure in question has a negative Poisson ratio. This ratio corresponds in practice to the ratio between the values of the dimensionless coefficients of dilation in mutually orthogonal directions caused by a tension acting in one of these directions, in particular the one whose coefficient of dilation forms the denominator of the ratio.

Conventional structures typically have a positive Poisson ratio. It has been commonly observed that a tensile force exerted along the longitudinal axis of a solid bar causes a contraction of its transverse direction. This behavior consequently makes the bar unstable when it is being bent and greatly limits the possibility of bending it through small radii of curvature.

In contrast, the inclusion in the prosthesis of the invention of a tubular member with auxetic behavior has a stabilizing effect when it is bent, with the result that it can also be bent through very small radii of curvature. It should be noted that this advantageous effect is of use both in the production of the prosthesis and during its use.

The auxetic behavior may be obtained by perforating the tubular member with apertures of desired shape, thus obtaining, for instance, re-entrant honeycomb cell structures (also called butterfly structures) or structures with two-dimensional chiral symmetry.

The prosthesis comprises a ring-shaped tubular member 18 having a longitudinal axis 20. The tubular member 18 (FIGS. 2 to 5) has a lateral wall formed by a plurality of columns of cells 22 disposed alongside one another (see in particular FIGS. 3 to 5 showing its plane development). Each cell 22 has a re-entrant honeycomb shape and is bounded by two rectilinear sides 24 which are parallel and of equal length and two substantially V-shaped sides 26 which join the facing ends of the two rectilinear sides and whose vertices 28 are directed towards one another. The cells 22 of adjacent columns are offset so that a rectilinear side 24 of a cell 22 of an adjacent column starts from the vertex 28 of each substantially V-shaped side 26 of a cell 22. The rectilinear sides 24 of the cells 22 are parallel to the longitudinal axis 20 of the tubular member 18.

In one embodiment, the ratio between the length of a rectilinear side 24 and its distance from the other rectilinear side 24 of the same cell 22 may be between about 0.2 and about 3. In one embodiment, this ratio is between about 0.25 and about 1.5.

In one embodiment, the ratio between the length of a rectilinear side 24 and the distance between the vertices 28 of the two substantially V-shaped sides 26 of the same cell 22 is greater than 1. In one embodiment, this ratio is between about 1.2 and about 2.5.

Figure 7:
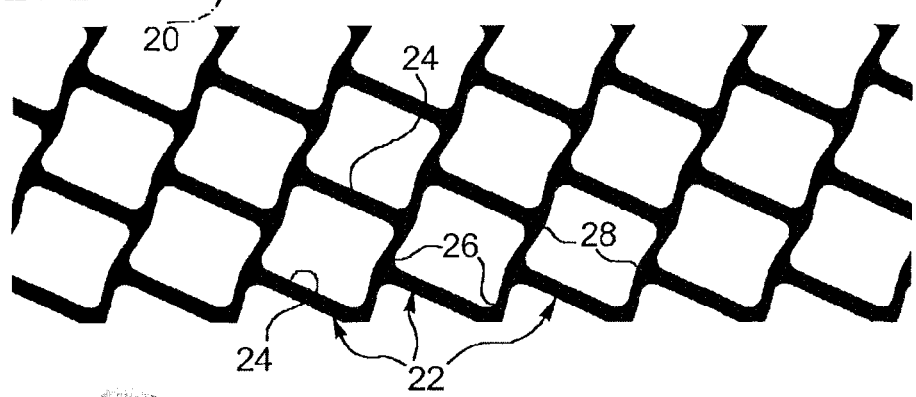
FIGS. 6 to 8 are views corresponding respectively to FIGS. 2, 4 and 5 of an alternative embodiment of the tubular member of the prosthesis of the invention.
Figure 8:
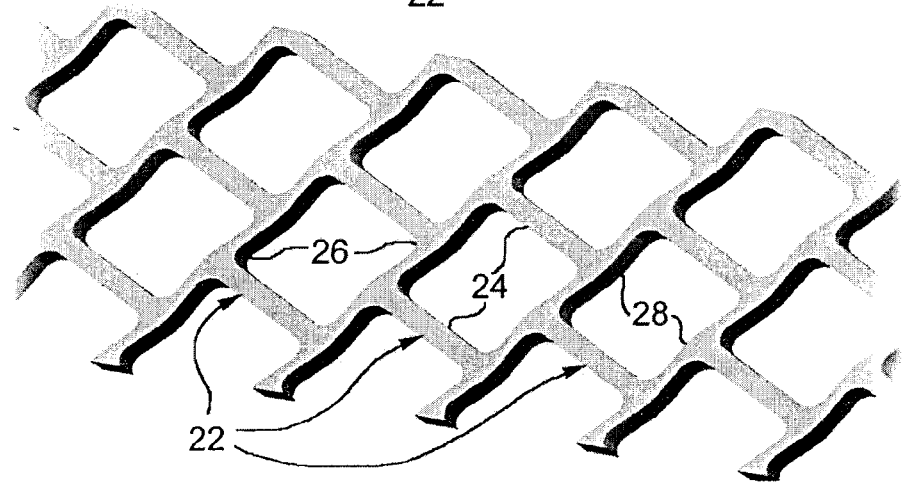
Figure 6:
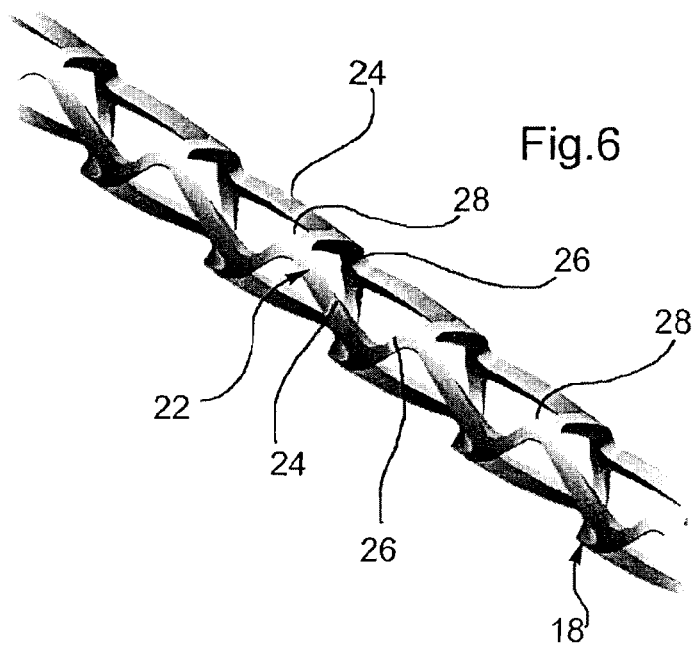

FIGS. 6 to 8 show an alternative embodiment of the tubular member, in which the same reference numerals as in the preceding figures are used to designate identical or equivalent components.

The only difference from the preceding embodiment consists in the fact that the rectilinear sides 24 of the cells 22 are slanted with respect to the longitudinal axis 20 of the tubular member 18. In various embodiments, the projection of each rectilinear side 24 of the cells 22 with respect to the plane parallel to this rectilinear side 24 passing though the longitudinal axis 20 may form, with this axis 20, an angle of between about 5° and about 45°. In one embodiment, this angle is between about 10° and about 30°.

Figure 9:
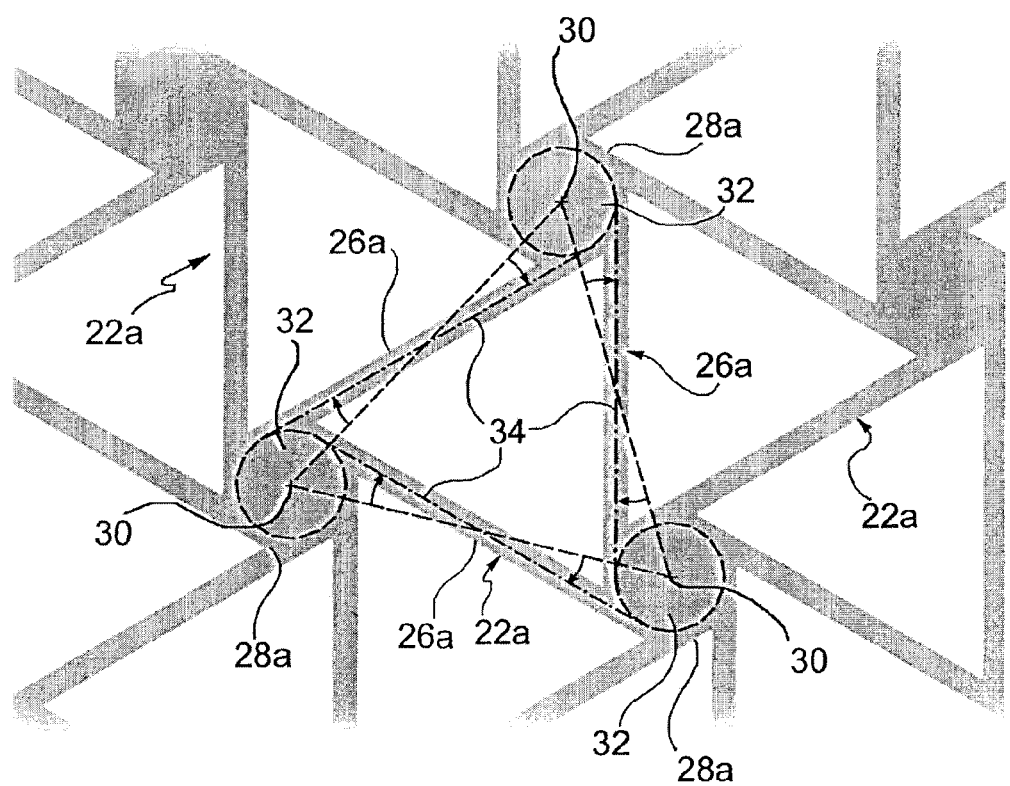
FIG. 9 is a diagrammatic plan view of the plane development of a portion of a further tubular member of the prosthesis of the invention of the type with two-dimensional chiral symmetry.

FIG. 9 shows, in outline, an alternative embodiment of the invention, in which the same reference numerals as in the preceding Figures are used to designate identical or equivalent components.

According to this embodiment, each of the cells 22a forming the lateral wall of the tubular member is bounded by three nodes 28a each having a center 30 and a peripheral region 32 and joined in pairs by an equal number of sides 26a. It should be borne in mind, however, that in embodiments of the invention which are not shown, the number of nodes and sides of each cell could be greater than three. Each side 26a joins the peripheral regions 32 of the respective nodes 28a and intersects the axis 34 joining the center 30 of these respective nodes 28a, but not the other sides 26a. The structure obtained in this way has two-dimensional chiral symmetry and also exhibits auxetic behavior.

FIGS. 10 to 12 show a particular embodiment of the tubular member having two-dimensional chiral symmetry as shown in diagrammatic form in FIG. 9.

In particular, the tubular member 18 has a lateral wall formed by a plurality of cells 22a, each of which is bounded by three substantially S-shaped sides 26a joined in pairs in three nodes 28a. Each cell 22a has three equal sides 26a and each of its nodes 28a is common to a node 28a of another five cells 22a.

In various embodiments, the ratio between the length of each substantially S-shaped side 26a and the distance between the two nodes 28a joined by this side may be between about 2 and about 10. In one embodiment, this ratio is between about 2.5 and about 5.

Figure 13:
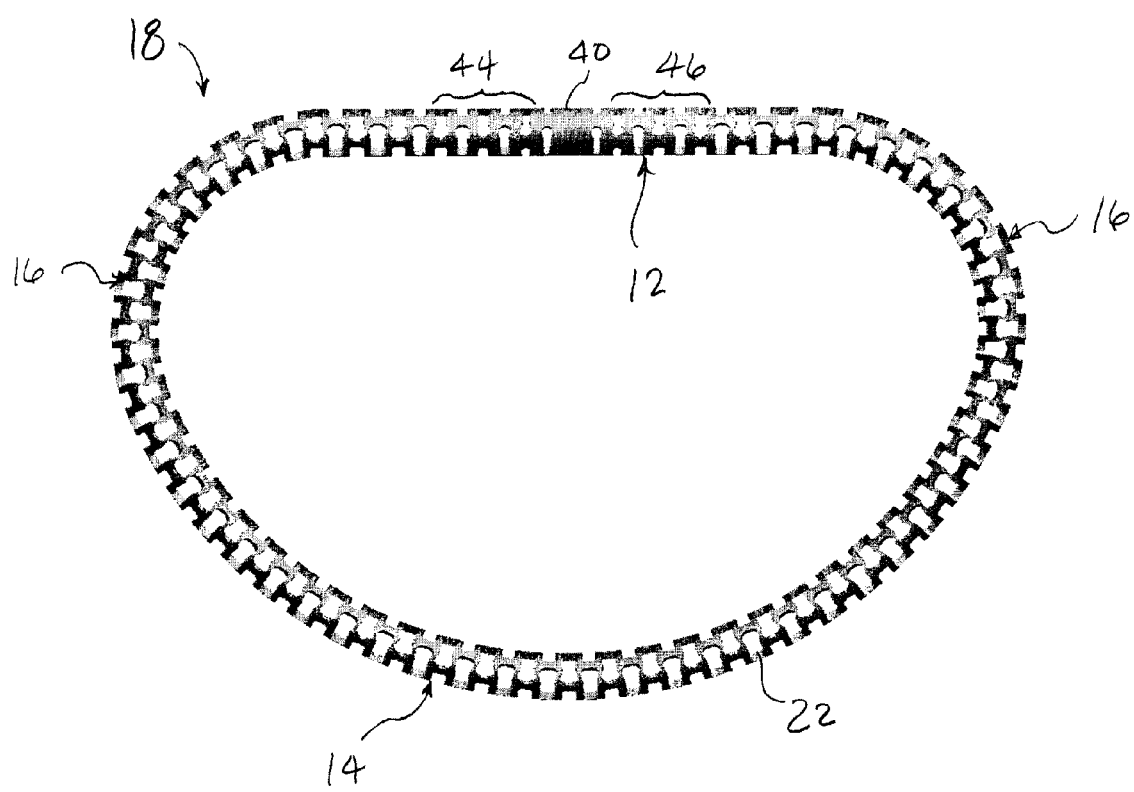
FIG. 13 is a plan view of a ring element of an annuloplasty prosthesis according to one embodiment of the present invention.

FIG. 13 is a plan view of the tubular member 18 including a plurality of columns of cells 22 having the re-entrant honeycomb shape shown in FIGS. 2-5 according to one embodiment of the present invention. As shown in FIG. 13, the cells 22 having the re-entrant honeycomb shape shown in FIGS. 2-5 are arranged along the longitudinal axis 20 (see FIG. 1) to define the curved sections 14, 16, and the end regions of the generally rectilinear or straight intertrigonal section 12. In the illustrated embodiment, the straight section 12 includes a center portion 40 having an uninterrupted wall (i.e., the wall is substantially devoid of any cells such as the cells 22). Additionally, in the illustrated embodiment, portions 44, 46 of the straight section 12 proximate the center portion 40 are defined by columns of cells having different overall geometries than the cells 22 defining the first and second curved sections 14, 16, such that the center portion 40 and the portions 44, 46 are generally stiffer than the first and second curved sections 14, 16. Thus, the flexibility of the tubular member 18, and thus the annuloplasty prosthesis 10, can be varied as desired along the longitudinal axis 20 (see FIG. 1) by varying the geometry and spacing of the cells of the tubular member 18.

Additionally, the flexibility of the prosthesis 10 can further be optimized for particular working conditions based on the positions of the individual cells 22 about the circumference of the tubular member 18. For example, in the embodiment illustrated in FIG. 13, the prosthesis 10 is assumed to undergo deflection under working conditions in the general plane of the annuloplasty prosthesis 10 as defined by the longitudinal axis 20, and the cells 22 are positioned such that one of the sides 24 of each column of cells 22 is positioned in and oriented along this general plane. Other cell configurations optimized for different working conditions may be utilized in various other embodiments.

The tubular member 18 may be manufactured using any suitable method. In one exemplary embodiment, cells of substantially uniform size and shape may be cut (e.g., by laser cutting) into a metallic tube (which may be made, without limitation, from a superelastic alloy such as nitinol or other suitable material), which is subsequently bent to form the D-shaped ring generally conforming to the shape of the natural cardiac valve annulus. The ends of the tube may be joined (e.g., by laser welding) and the tube member 18 may be heat set, depending on the material used. In one embodiment, the cells 22 may have a size and shape prior to bending substantially similar to the cells in the portions 44, 46. In such embodiment, bending the tube into the shape of the annuloplasty prosthesis 10 causes the cells 22 to assume their final shape as shown in FIG. 13. In other embodiments, the tubular member 18 may be made using other methods.

The surface of the tubular member 18 may be coated by a sheath of biocompatible material selected, for instance, from the group including polymers, synthetic tissues, biological tissues and their combinations. The surfaces of the ring member and/or the sheath may in turn be coated with haemocompatible carbon, for instance turbostratic carbon. The method of production of this material is disclosed, for instance, in U.S. Pat. Nos. 5,084,151, 5,387,247, 5,370,684, 5,133,845 and 5,423,886 in the name of the same applicant. This coating helps to make the prosthesis more haemocompatible and contributes to controlled tissue growth of the recipient organism.

The inner cavity of the tubular member may also be filled with elastomer material, for instance silicone, polyurethane or their mixtures, as disclosed in European Patent Application EP-A-1 266 641 in the name of the same applicant.

Without prejudice to the principle of the invention, details and embodiments may obviously be widely varied with respect to what has been described and illustrated by way of example, without thereby departing from the scope of the invention claimed. In particular, the tubular member may be open and therefore not of a closed ring shape and/or its lateral wall could have any other kind of cell geometry provided that its relative Poisson ratio remains negative. The auxetic behavior could, moreover, relate solely to a part of the tubular member, while the remaining part could be embodied in a conventional manner.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. An annuloplasty prosthesis for implantation in a cardiac valve annulus, the prosthesis comprising a tubular member having a size and shape generally corresponding to a shape of the cardiac valve annulus and including a longitudinal axis, a straight section having first and second ends, and a first curved section between the first and second ends, the first curved section and at least part of the straight section including a plurality of columns of cells disposed along the longitudinal axis, wherein each column of cells consists of three cells positioned about the longitudinal axis, and wherein the cells are sized and shaped such that the first curved section and the at least part of the straight section are configured to exhibit an auxetic behavior when subject to a tensile stress along the longitudinal axis, wherein at least some of the cells in the at least part of the straight section differ in size or shape from the cells in the first curved section such that the at least part of the straight section has a different flexibility than the first curved section.

2. The annuloplasty prosthesis of claim 1 wherein the cells in at least the first curved section are substantially uniform in shape and size.

3. The annuloplasty prosthesis of claim 1 wherein each cell is defined by opposed first and second sides each having a first end, a second end, and a straight portion therebetween, a substantially V-shaped third side connecting the first ends of the first and second sides, and a substantially V-shaped fourth side connecting the second ends of the first and second sides, the substantially V-shaped third and fourth sides each having a vertex directed toward the other substantially V-shaped side.

4. The annuloplasty prosthesis of claim 3 wherein the cells of adjacent columns are circumferentially offset such that the straight portions of the first and second sides of the cells of a respective column of cells extend between the vertices of the V-shaped sides of the cells of the adjacent columns of cells.

5. The annuloplasty prosthesis of claim 4 wherein the straight portions of the first and second sides of the cells of each respective column of cells are arranged substantially parallel to each other.

6. The annuloplasty prosthesis of claim 5 wherein the longitudinal axis defines a general plane of the prosthesis, and further wherein the first side of one of the cells in each column is positioned in the general plane of the prosthesis.

7. The annuloplasty prosthesis of claim 3 wherein the straight portions of the first and second sides of the cells are arranged substantially parallel to the longitudinal axis.

8. The annuloplasty prosthesis of claim 3 wherein the straight portions of the first and second sides of the cells are arranged at an angle with respect to the longitudinal axis.

9. The annuloplasty prosthesis of claim 1 wherein the tubular member further includes a second curved section between the first end of the straight section and the first curved section, and a third curved section between the second end of the straight section and the first curved section, the second and third curved sections exhibiting an auxetic behavior when subject to a tensile stress along the longitudinal axis.

10. The annuloplasty prosthesis of claim 9 wherein the plurality of columns of cells are disposed along the longitudinal axis so as to define the second and third curved sections and at least part of the straight section.

11. The annuloplasty prosthesis of claim 10 wherein the cells defining the first, second and third curved sections are substantially uniform in size and shape.

12. An annuloplasty prosthesis comprising a tubular member having a longitudinal axis and a size and a shape generally corresponding to a natural cardiac valve annulus and including a longitudinal axis, a straight section having first and second ends, and a curved section between the first and second ends, wherein at least one of the sections of the tubular member is defined by a plurality of columns of cells disposed along the longitudinal axis, wherein each column of cells consists of three cells positioned about the longitudinal axis, and wherein the cells are sized and shaped such that the at least one of the sections of the tubular member exhibits an auxetic behavior, and wherein some of the cells in adjacent columns of cells differ in size so as to vary the flexibility of the at least one of the sections along its length.

13. The annuloplasty prosthesis of claim 12 wherein the tubular member is in the shape of a substantially D-shaped ring.

14. The annuloplasty prosthesis of claim 12 wherein the cells have a re-entrant honeycomb shape.

15. An annuloplasty prosthesis for implantation in a cardiac valve annulus, the prosthesis comprising a tubular member having a size and a shape generally corresponding to a shape of the cardiac valve annulus and including a longitudinal axis, a straight section having first and second ends, and a first curved section between the first and second ends, the first curved section and at least part of the straight section including a plurality of columns of cells, wherein each column of cells consists of three cells positioned about the longitudinal axis, and wherein each cell includes opposing rectilinear sides and opposing V-shaped sides, disposed along the longitudinal axis such that the first curved section and the at least part of the straight section are configured to exhibit an auxetic behavior when subject to a tensile stress along the longitudinal axis, wherein each of the rectilinear sides is disposed in a plane oriented generally parallel to a plane of the prosthesis, and wherein some of the cells in the at least part of the straight section differ in size such that the flexibility of the at least part of the straight section varies along its length.

* * * * *